US00PP31499P2

(12) United States Plant Patent
Egger

(10) Patent No.: US PP31,499 P2
(45) Date of Patent: Feb. 25, 2020

(54) ***PENSTEMON* PLANT NAMED 'TNPENHR'**

(50) Latin Name: ***Penstemon* hybrid**
Varietal Denomination: TNPENHR

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/350,947

(22) Filed: Feb. 4, 2019

(51) Int. Cl.
*A01H 5/02* (2018.01)
*A01H 6/68* (2018.01)

(52) U.S. Cl.
USPC ..... Plt./465
CPC ..... *A01H 6/68* (2018.05)

(58) Field of Classification Search
USPC ..... Plt./465
See application file for complete search history.

*Primary Examiner* — Anne Marie Grunberg
(74) *Attorney, Agent, or Firm* — Klarquist Sparkman, LLP

(57) ABSTRACT

A new and distinct cultivar of *Penstemon* plant is characterized by medium-size red flowers in dense clusters; long bloom time; good rebloom; a compact, upright, well-branched habit with multiple crowns from the base; clean-looking, deep-green, attractive foliage; and excellent vigor.

1 Drawing Sheet

Botanical denomination: *Penstemon* hybrid.
Variety designation: 'TNPENHR'.

BACKGROUND OF THE INVENTION

The present invention relates to a new and distinct cultivar of *Penstemon* given the name 'TNPENHR'. *Penstemon* is in the family Scrophulariaceae. *Penstemon* 'TNPENHR' originated as open pollinated seed collected from *Penstemon* '262-1', an unnamed, unpatented, proprietary plant. It was part of a controlled breeding program to create a compact, upright, medium-small-size-habit, reblooming, and hardy series. This seedling was selected for its medium-size red flowers in dense clusters; long bloom time; good rebloom; compact, upright, well-branched habit with multiple crowns from the base; vigor; and clean, attractive look. It is an ideal plant for a sunny border in full sun.

SUMMARY OF THE INVENTION

The present invention has not been evaluated under all possible environmental conditions. The phenotype may vary with variations in environment without a change in the genotype of the plant.

*Penstemon* 'TNPENHR' is uniquely distinguished by its:

1. medium-size red flowers in dense clusters,
2. long bloom time,
3. good rebloom,
4. compact, upright, well-branched habit with multiple crowns from the base,
5. clean-looking, deep-green, attractive foliage, and
6. excellent vigor.

Compared to the seed parent, *Penstemon* '262-1', the new cultivar is more floriferous and upright, rather than floppy.

Compared to *Penstemon* 'Cha Cha Cherry', U.S. Plant Pat No. 28,163, the new cultivar has smaller flowers, smaller and narrower leaves, and a shorter habit.

Compared to *Penstemon* 'Sunburst Ruby', an unpatented seed variety, the new cultivar has larger flowers in denser inflorescences and is more upright.

Trade Designation: HARLEQUIN™ Red.

The new variety has been reproduced only by asexual propagation (cuttings and micropropagation). Each of the progeny exhibits identical characteristics to the original plant. Asexual propagation by cuttings and micropropagation using terminal and lateral shoots, as done in Canby, Oreg., shows that the foregoing characteristics and distinctions come true to form and are established and transmitted through succeeding propagations.

DETAILED PLANT DESCRIPTION

Figure 1:
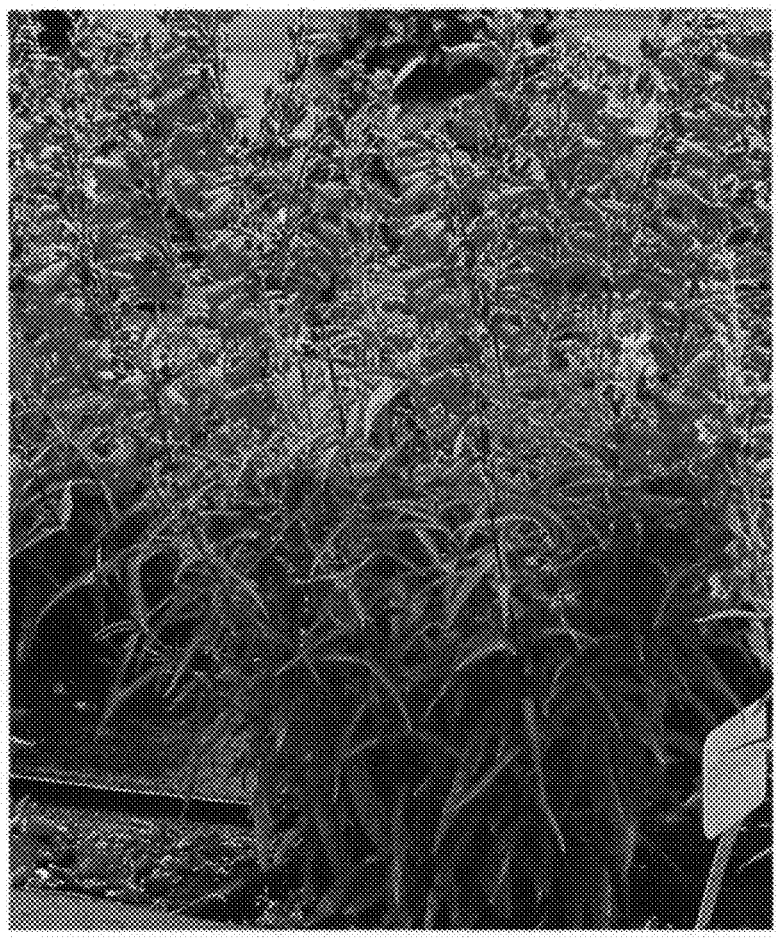
FIG. 1 shows a close up of the new cultivar as a 12-month-old in a trial field in full bloom in mid-August in Canby, Oreg.
Figure 2:
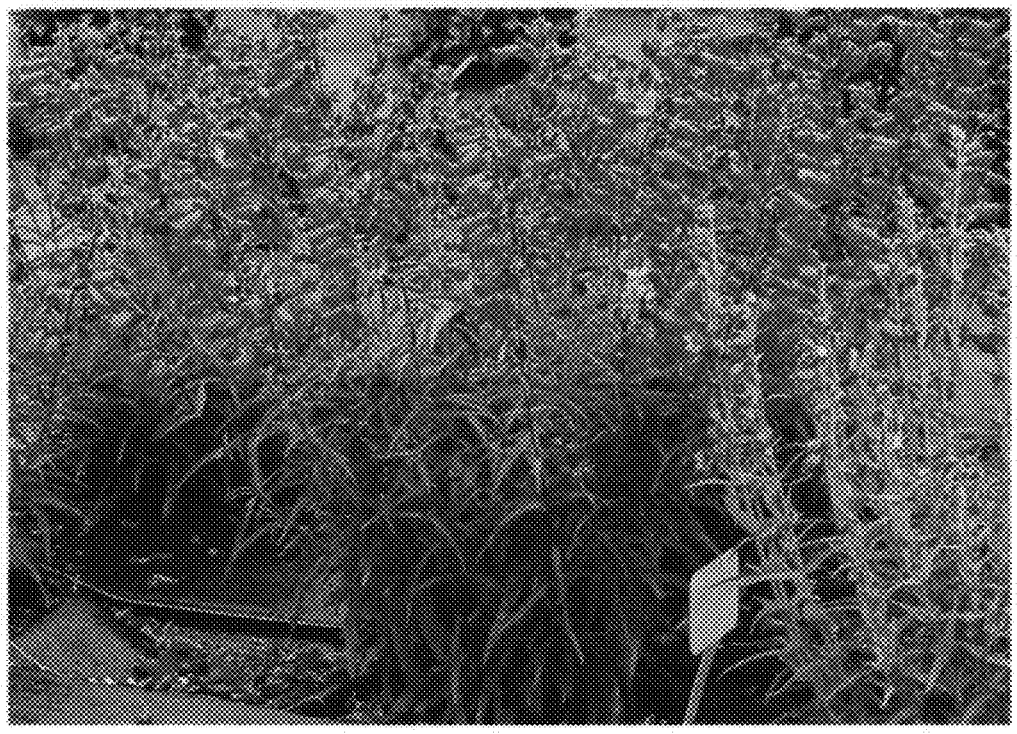
FIG. 2 shows the habit of a new cultivar as 12-month-old plant in the trial field in full bloom in August in Canby, Oreg.

The following is a detailed description of the new *Penstemon* cultivar based on observations of two-year old specimens grown outside in a trial field in full sun in Canby, Oreg. in October. Canby is Zone 8 on the USDA Hardiness map. Temperatures range from a high of 95° F. in August to an average of 32° F. in January.

Normal rainfall in Canby is 42.8 inches per year. The color descriptions are all based on The Royal Horticultural Society Colour Chart, 5$^{th}$ edition, 2007.

Plant:

*Type.*—Herbaceous perennial.
*Form.*—Upright, branching.
*Cold Hardiness.*—USDA Zone 6-10.
*Size.*—Grows to 40 cm wide and 50 cm high.
*Vigor.*—Excellent.

*Stem number.*—About 16 main stems from the crown.
*Stem strength.*—Strong.
*Stem.*—Strongly upright, branched, grows to 25 cm long to the main inflorescence and 4 mm wide (at the base), glabrous, internodes grow to 2.5 cm long, Yellow Green 146C to Grey Brown 199C at base.
*Roots and rooting.*—Fibrous root system, White 155C, roots easily from stem cuttings in 10 to 14 days.

Leaf:
*Type.*—Simple.
*Arrangement.*—Opposite.
*Shape.*—Lanceolate.
*Blade size.*—Grows to 7.2 cm long and 6 mm wide.
*Venation.*—Pinnate, main vein on top Yellow Green 147B and bottom side Yellow Green 147C.
*Margins.*—Entire to serrulate.
*Apex.*—Acuminate.
*Base.*—Sessile.
*Petiole.*—None, sessile.
*Surface texture.*—Glabrous on both sides.
*Leaf color.*—Topside Green 137B, bottom side closest to Yellow Green 147B.

Inflorescence:
*Type.*—Terminal, many flowered, dense thyrse.
*Number offlowers per inflorescence.*—20 to 54.
*Size of inflorescence.*—Grows to 21 cm long and 10 cm wide.
*Peduncle.*—Strong, upright, grows to 2 cm long and 3 mm wide, glandular pubescent, Yellow Green 146B tinted Greyed Purple 187A in sun.
*Pedicel.*—Medium strength, grows upright to 5 mm long and 1 mm wide, glandular pubescent, Yellow Green 146C in shade and tinted Greyed Purple 187A in sun.
*Bloom period.*—Mid-June to frost in November in Canby, Oreg. if spent flowers are removed.

Flower bud:
*Size.*—2.8 cm long and 10 mm wide.
*Description.*—Closed tubular, bulging, flattened centrically, pubescent.
*Color.*—Red 53B darkening to 53A on tip.

Flower:
*Type.*—Zygomorphic, perfect.
*Shape.*—Tubular, bilabiate.
*Size.*—Grows to 3.5 cm long and 2.7 cm wide.
*Corolla description.*—Grows to 3.5 cm long and 2.7 cm wide; tube is bulbous in the calyx for 5 mm long and 5 mm wide, narrowing then widening for 20 mm and flaring to 12 mm wide; 5 lobes, the top lobe and side 2 lobes are 10 mm wide and 10 mm long, the bottom 2 lobes are 10 mm wide and 10 mm long, lobe margins entire, and tips obtuse; outside glandular pubescent, inside sparsely pubescent; outside color Red 53B, inside color lobes Red 53B, tube Red 49C on top and Red 49C streaked with Greyed Purple 187A on bottom and sides.
*Calyx description.*—13 mm deep and 14 mm wide, 5 lobes cut to the base; lobes lanceolate, 12 mm deep and 4 mm wide; margins entire to occasionally incised; tip acuminate; base cuneate; outside Greyed Purple 187A; inside Yellow Green 147B with margins Greyed Purple 187A; both sides pubescent.
*Pistil description.*—1, 21 mm long, ovary 4 mm long and 2 mm wide, Yellow Green 147B; style 17 mm long and less than 1 mm wide, style White NN155C; stigma flattened, White NN155C.
*Stamen description.*—5, one sterile without an anther, held within the corolla 25 mm long; filaments 18 to 26 mm long and less than 1 mm wide, White NN155C tinted Greyed Purple 187B; anthers horseshoe-shaped, 2 mm long and 2 mm wide, Greyed Purple 187B; pollen amount moderate, White NN155C.
*Fragrance.*—None.
*Lastingness.*—A flower lasts 5 to 6 days.

Fruit:
*Type.*—Capsule.
*Fertility.*—Poor.
*Size.*—7 mm deep and 5 mm wide.
*Texture.*—Glabrous.
*Color.*—Brown N199C.

Seed:
*Shape.*—Irregular.
*Size.*—1 mm long.
*Texture.*—Glabrous.
*Color.*—Brown 200A.

Pests and diseases: The new cultivar is typical to the genus. No problems have been found in Canby, Oreg.

I claim:

1. A new and distinct *Penstemon* plant as illustrated and described.

* * * * *